(12) United States Patent
Hsueh et al.

(10) Patent No.: US 9,903,800 B2
(45) Date of Patent: Feb. 27, 2018

(54) MEASUREMENT OF FRACTURE TOUGHNESS OF HETEROGENEOUS MATERIALS

(71) Applicant: CALIFORNIA INSTITUTE OF TECHNOLOGY, Pasadena, CA (US)

(72) Inventors: Chun-Jen Hsueh, Pasadena, CA (US); Kaushik Bhattacharya, La Canada, CA (US); Guruswami Ravichandran, Arcadia, CA (US); Md Z. Hossain, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/182,168

(22) Filed: Jun. 14, 2016

(65) Prior Publication Data

US 2016/0370269 A1 Dec. 22, 2016

Related U.S. Application Data

(60) Provisional application No. 62/180,387, filed on Jun. 16, 2015.

(51) Int. Cl.
*G06K 9/00* (2006.01)
*G01N 3/08* (2006.01)
*G06T 7/00* (2017.01)

(52) U.S. Cl.
CPC ............ *G01N 3/08* (2013.01); *G06T 7/0002* (2013.01); *G01N 2203/0066* (2013.01); *G01N 2203/0218* (2013.01); *G01N 2203/0647* (2013.01); *G06T 2207/30164* (2013.01)

(58) Field of Classification Search
None
See application file for complete search history.

(56) References Cited

U.S. PATENT DOCUMENTS

| | | | | |
|---|---|---|---|---|
| 4,502,337 A | * | 3/1985 | Archer | G01B 5/30 73/762 |
| 4,574,642 A | * | 3/1986 | Fleischman | G01N 3/32 73/799 |
| 5,005,423 A | * | 4/1991 | Poormon | G01N 3/32 73/799 |
| 5,539,656 A | * | 7/1996 | Annigeri | G01N 3/02 356/23 |

(Continued)

OTHER PUBLICATIONS

Hsueh, Chun-Jen, Kaushik Bhattacharya, Guruswami Ravichandran, and Md Z. Hossain. "Measurement of fracture toughness of heterogeneous materials." The Society for Experimental Mechanics, Inc. 2016 A.M. Beese et al. (eds.), Fracture, Fatigue, Failure and Damage Evolution, vol. 8, Conference Proceedings of the Society for Experimental Mechanics Seri.*

(Continued)

*Primary Examiner* — Andrae S Allison
(74) *Attorney, Agent, or Firm* — Steinfl + Bruno LLP

(57) ABSTRACT

Methods for measuring the effective fracture toughness in a material are described. A rail and roller system are used to apply a gradual force to a specimen. The time-dependent force creates a steady fracture development that allows a camera to record the progressive fracture in the material. Mathematical methods can then be used to analyze the fracture progression and determine the effective fracture toughness.

20 Claims, 7 Drawing Sheets

(56) References Cited

U.S. PATENT DOCUMENTS

| | | | | |
|---|---|---|---|---|
| 5,602,329 | A * | 2/1997 | Haubensak | G01N 3/08 73/105 |
| 7,538,891 | B1 * | 5/2009 | Mello | G01B 11/2441 356/35.5 |
| 2012/0287248 | A1 * | 11/2012 | Erdman III | G01N 3/068 348/47 |
| 2014/0026635 | A1 * | 1/2014 | Zorn | G01N 3/24 73/12.06 |
| 2015/0274587 | A1 * | 10/2015 | Barthelat | C03B 33/04 29/428 |
| 2016/0061748 | A1 * | 3/2016 | Handler | G01N 21/255 356/402 |
| 2016/0131564 | A1 * | 5/2016 | Hossain | G01N 3/40 73/799 |

OTHER PUBLICATIONS

APC Z. Burghard et al.: 'Crack opening profiles of indentation cracks in normal and anomalous glasses' Acta Mater. vol. 52, 2004, pp. 293-297.*

Pallares et al, Crack opening profile in DCDC specimen, Int J Fract (2009) 156:11-20.*

Mathieu et al, Identification of a crack propagation law by digital image correlation, International Journal of Fatigue 36 (2012) 146-154.*

Roux et al, Stress intensity factor measurements from digital image correlation: post-processing and integrated approaches, International Journal of Fracture (2006) 140:141-157.*

Roux et al, Digital image correlation and fracture: an advanced technique for estimating stress intensity factors of 2D and 3D cracks, Journal of Physics D: Applied Physics , Appl. Phys. 42 (2009).*

P. Lorenzino, Application of Digital Image Correlation (DIC) in resonance machines for measuring fatigue crack growth, Focussed on: Fracture and Structural Integrity related Issues (2014).*

Badulescu, C. et al., "Investigation of the Grid Method for Accurate In-Plane Strain Measurment.", Meas. Sci. Technol., vol. 20, 095102, (2009), 18 pages.

Bower, A.F. et al., "A Three-Dimensional Analysis of Crack Trapping and Bridging Tough Particles.", J. Mech. Phys. Solids, vol. 39, No. 6, pp. 815-858, (1991), 44 pages.

Cox, B. et al., "In Quest of Virtual Tests for Structural Composites.", Science, vol. 314, pp. 1102-1107, Nov. 2006, 7 pages.

Faber, K.T. et al., "Crack Deflection Processes-I. Theory.", Acta Metallurgica., vol. 31, No. 4, pp. 565-576, (1983), 12 pages.

Gao, H. et al., "A First-Order Perturbation Analysis of Crack Trapping by Arrays of Obstacles.", Journal of Applied Mechanics, vol. 56, pp. 828-836, (1989), 10 pages.

Hossain, M.Z. et al., "Effective Toughness of Heterogeneous Media.", Journal of the Mechanics and Physics of Solids, vol. 71, pp. 15-32, (2014).

Hutchinson, J.W. et al., "Mixed Mode Cracking in Layered Materials.", Advances in Applied Mechanics, vol. 29, pp. 63-191, (1992), 130 pages.

Kruzic, J.J. et al., "The Utility of R-Curves for Understanding Fracture Toughness-Strength Relations in Bridging Ceramics." J. Am. Ceram. Soc., vol. 91, No. 6, pp. 1986-1994, (2008), 11 pages.

Liang, F., et al., "Fracture Behavior of Flock Fiber Reinforced Laminar Composite." Journal of Materials Science and Engineering B, 2011. 1(1), 2 pages. (Abstract Only).

* cited by examiner

MEASUREMENT OF FRACTURE TOUGHNESS OF HETEROGENEOUS MATERIALS

CROSS REFERENCE TO RELATED APPLICATIONS

The present application claims priority to U.S. Provisional Patent Application No. 62/180,387, filed on Jun. 16, 2015, and may be related to U.S. patent application Ser. No. 14/937,634, filed Nov. 10, 2015 and published May 12, 2016 (US 2016/0131564 A1), the disclosures of both of which are incorporated herein by reference in their entirety.

STATEMENT OF INTEREST

This invention was made with government support under Grant No. CMMI1201102 awarded by the National Science Foundation. The government has certain rights in the invention.

TECHNICAL FIELD

The present disclosure relates to toughness testing. More particularly, it relates to measurement of fracture toughness of heterogeneous materials.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
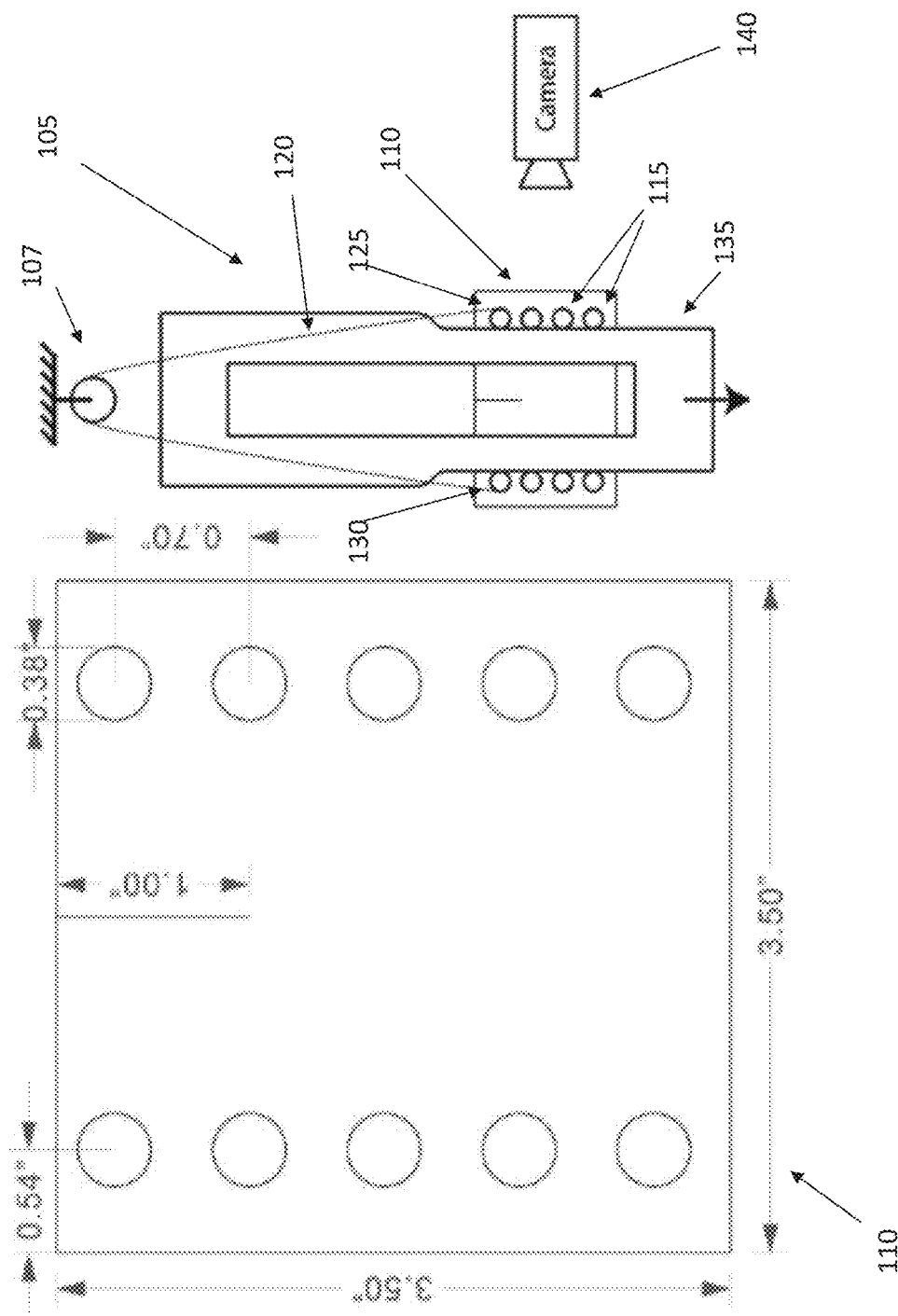
FIG. 1 illustrates a homogeneous specimens dimension and experiment configurations.

In a first aspect of the disclosure, a method is described, the method comprising: providing a specimen comprising at least a first and second hole; inserting a first rod into the first hole and a second rod into the second hole; attaching a first end of a cable to the first rod and a second end of the cable to the second rod; providing a cable support; placing a portion of the cable on the cable support; providing a rail, the rail comprising at least two sloped regions angled away from a longitudinal axis and configured to laterally displace the first and second rod relative to each other; inserting the specimen in the rail; and applying a time-dependent displacement boundary condition to the specimen by gradually moving the rail away from the cable support, thereby applying a displacing force to the first and second rods through the at least two sloped regions and causing the specimen to fracture In a second aspect of the disclosure, a method is described, the method comprising: providing a specimen comprising at least a first and second hole; inserting a first rod into the first hole and a second rod into the second hole; attaching the first rod and the second rod to rigid linkage arms; providing a rail, the rail comprising at least two sloped regions angled away from a longitudinal axis and configured to laterally displace the first and second rod relative to each other; inserting the specimen in the rail; and applying a time-dependent displacement boundary condition to the specimen by gradually moving the rail and the specimen relative to each other, thereby applying a displacing force to the first and second rods through the at least two sloped regions and causing the specimen to fracture.

DETAILED DESCRIPTION

The present disclosure describes methods to measure the effective fracture toughness of heterogeneous materials. Specifically, methods are described to apply surfing boundary conditions to specimens by using a rail and roller to apply surfing boundary condition on specimens. The roller slides on the rail and the surfing boundary condition (depending on the rail shape) is applied. Unlike conventional methods, which apply loads at fixed positions at the same time, the present disclosure describes methods that allow the rail to apply displacements sequentially to certain points of the specimen, thereby having a stable fracture growth.

Therefore, the present disclosure describes how to steadily control the fracture propagation in the material at a macroscopic level. This method also allows microscopic analysis of the fracture. According to the present disclosure, there is no requirement to weaken a plane to control the likely path of the fracture. Another advantage of the present disclosure is that the methods described herein can be integrated with any full-field measurement methods, e.g. Digital image correlation (DIC), grid methods . . . etc. Therefore, it is possible to perform the full-field measurement and characterize the fracture growth quantitatively.

Heterogeneous materials, where the scale of the heterogeneities is small compared to the scale of applications, are common in nature. These materials are also engineered synthetically with the aim of improving performance. The overall properties of heterogeneous materials can be different from those of its constituents; however, it is challenging to characterize effective fracture toughness of these materials. The present disclosure describes methods for experimentally determining the effective fracture toughness. The concept is to impose a steady process at the macroscale while allowing the fracture process to freely expand at the microstructure level. A time-dependent displacement boundary condition, called the surfing boundary condition, is applied. This boundary condition corresponds to a steadily propagating macroscopic crack opening displacement. It is then possible to measure the full-field displacement with the digital image correlation (DIC) method, and use it to obtain the macroscopic energy release rate. In particular, it is possible to develop a global approach to extract information from DIC. The effective toughness is obtained at the peak of the energy release rate. The full field images also provide insight into the role of the microstructure in determining effective toughness.

As known to the person of ordinary skill in the art, there are several experimental methods for measuring the fracture toughness of homogeneous materials, including single edge notch tension (SENT), center cracked tension (CCT), ASTM standard compact tension (CT), and single edge notch bend (SENB), see Ref. [1]. However, general methods for measuring the toughness of heterogeneous materials remain less well developed, though there are well-established methods for specific materials such as the double cantilever beam (DCB) method for the laminar material (see Ref. [2]) or r-curve measurement of ceramics, see Ref. [3]. Similarly, a systematic understanding of the effective toughness and how it depends on microstructure also remains a topic of active research, see Refs. [4-8]. Recently, Hossain et al., see Ref. [9], proposed an approach to defining the effective toughness of brittle heterogeneous materials and used it to study the role of microstructure in determining overall toughness. The present disclosure describes results of a new experimental method to measure the toughness of heterogeneous materials based on the theoretical work of Hossain et al. The concept is to enforce a macroscopically steady crack growth while allowing crack deflection, pinning, nucleation of distal cracks etc. at the microscopic scale, while measuring the macroscopic energy release rate.

In the present disclosure, an experimental configuration is described to enable a steady and controlled crack growth at the macroscopic scale without imposing any constraints at the microscopic scale. An exemplary configuration is shown in FIG. 1 (105). A specimen can be cut from ⅛" thick Homalite H-911 sheets using a laser cutter. An exemplary specimen is illustrated in FIG. 1 (110). Rods can be inserted into the specimen (110). The rods (115) are attached to a specifically shaped pair of rail with rollers. The first rod (125) is connected to another roller (130) with cables (120) for self-alignment and the rail is attached on a linear stage (135). The linear stage (135) pulls the rail downwards while the specimen is held fixed by the cables (120). In some embodiments, the rail is moved by a stepper motor. As a result of the shape of the rails, when the linear stage pulls the rail down, the specimen slides along the rail and the rail imposes a smoothly translating crack-opening displacement that approximates the surfing boundary conditions proposed by Hossain et al. in Ref. [9].

It is then possible to determine the macroscopic energy release rate by measuring the macroscopic stress intensity factor. More precisely, assuming the existence of a K-dominant region, the digital image correlation (DIC) method can be used. A random fine speckle pattern can be applied on the specimens. When the specimen is deformed, a CCD camera (140) observes the deformation of the pattern. A global data analysis method can then be used to calculate the stress intensity factor.

Figure 2:
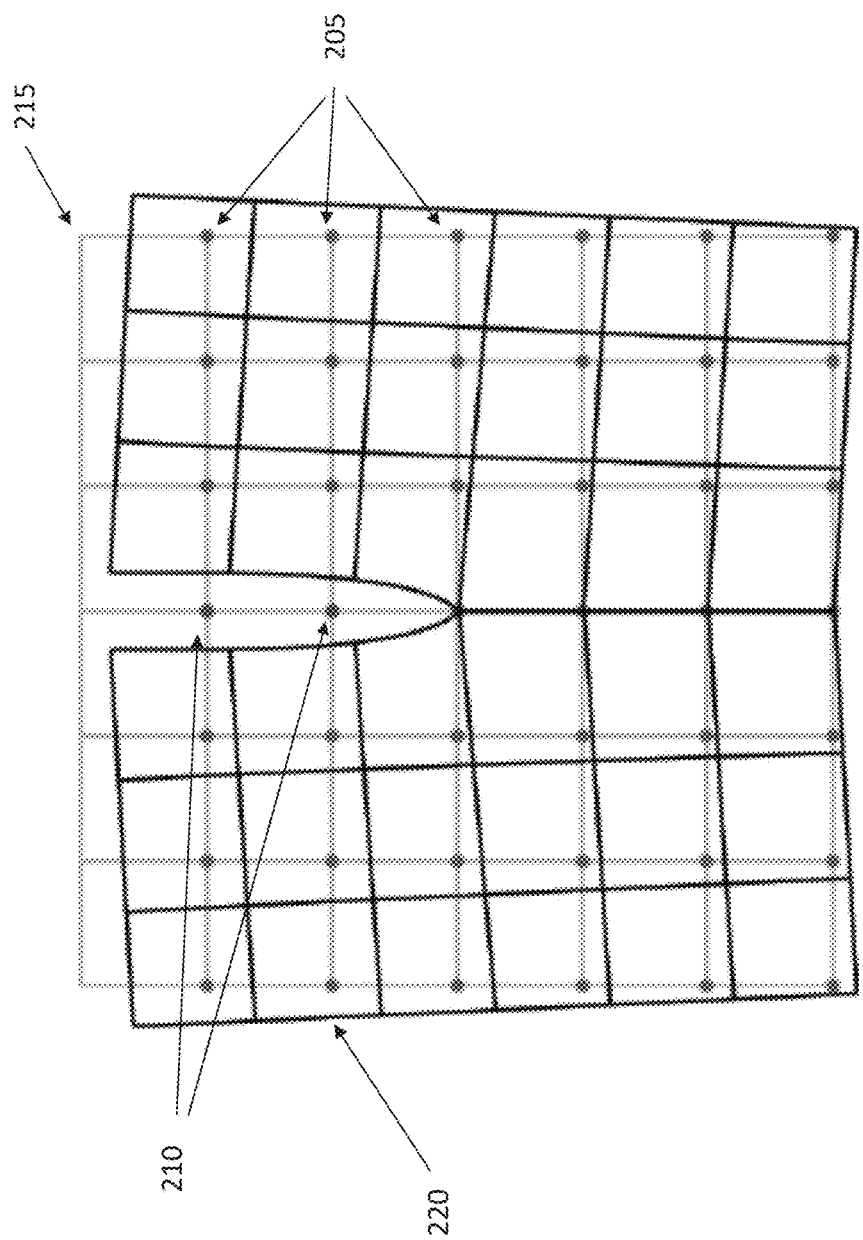
FIG. 2 illustrates a reference mesh and a deformed mesh.

The grey level in the deformed image g(x) is related to the grey level in the reference image f(x) by $$f(x)=g(x+u(x))$$

where u(x) is the displacement field in reference configuration, see Ref. [10]. It is also known that the mode-I asymptotic displacement field is $$u(x; K_I, x_0) = \frac{K_I}{2\mu}\sqrt{\frac{r}{2\pi}} U(\theta; k)$$

where μ,K corresponds to the material properties, r,θ is the polar coordinate with origin coinciding with crack tip position $x_0$, θ=0 coincides with the crack propagation direction, and $K_I$ is the stress intensity factor, see Ref [1]. Thus it is possible to calculate the deformed position of each pixel for a reference image f(x) with given stress intensity factor $K_I$ and crack tip position $x_0$. Linear interpolation can then be applied to establish the grey value for the points that are enclosed in the deformed meshes, dots (205) in FIG. 2. It is possible to use background values for the points that are not enclosed in the deformed meshes, dots (210) in FIG. 2. In FIG. 2, the deformed mesh (220) and the not deformed mesh (215) are visible. Following the steps above, it is possible to calculate the deformed reference image $g(x; K_I, x_0)$.

A cost function can be defined as the difference between the experimental observation and the deformed reference image, as is shown in the following equation:

$$\int_\Omega \|G(x) - g(x; K_I, x_0)\|^2 d\Omega$$

where G(x) is the experiment observation and $g(x; K_I, x_0)$ is the deformed reference image with given stress intensity factor and crack tip position. Minimizing the cost function above with respect to $K_I$ and $x_0$ gives us the optimal stress intensity factor and the optimal crack tip position.

The person of ordinary skill in the art will know that the following optimization problem is not convex in general.

$$\min_{x_0, K_I} \int_\Omega \|G(x) - g(x; K_I, x_0)\|^2 d\Omega$$

Figure 3:
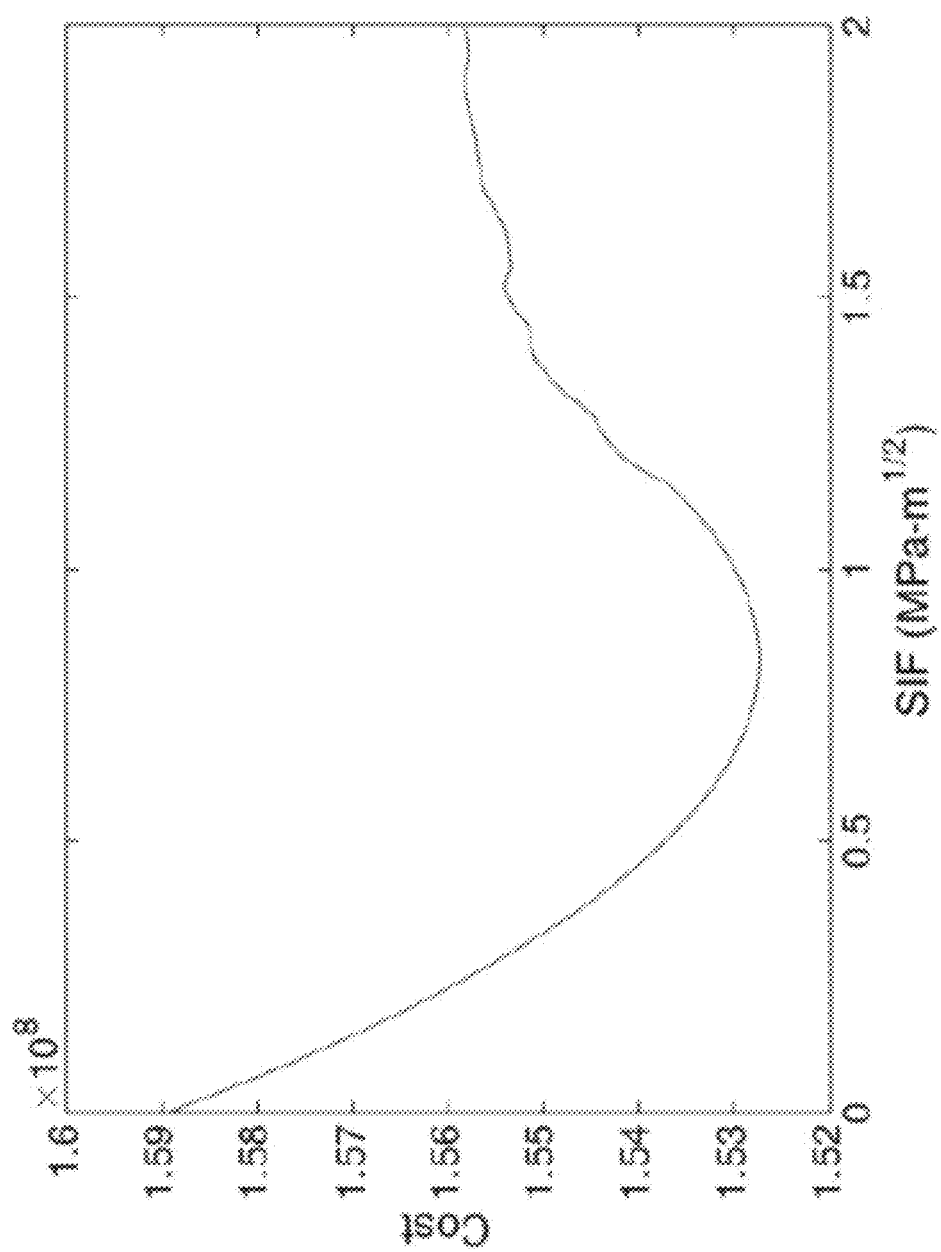
FIG. 3 illustrates a graph with cost vs. stress intensity factor with a fixed crack tip position.

However, when the cost function is plotted versus the stress intensity for a fixed crack tip position $x_0$, as visible in FIG. 3, it is possible to see that the function is convex when the stress intensity factor is smaller than a certain critical value. Thus it is necessary to establish the minimum value for a given crack tip position when the initial guess is small enough. In the following sections, the expression 0.5 MPa √m was used as initial guess.

To calculate the optimal pair ($K_I$, $x_0$), the deformed reference image was compared to the experiment observation image and an initial guess $x_{CE0}$ was made for the crack tip position. A region A was then constructed, with initial guess $x_{CE0}$ as the center. For every crack tip position contained in region A, it is possible to calculate the corresponding optimal stress intensity factor and the cost function. On the basis of these calculations, the optimal pair with the minimum cost function was chosen.

Figure 4:
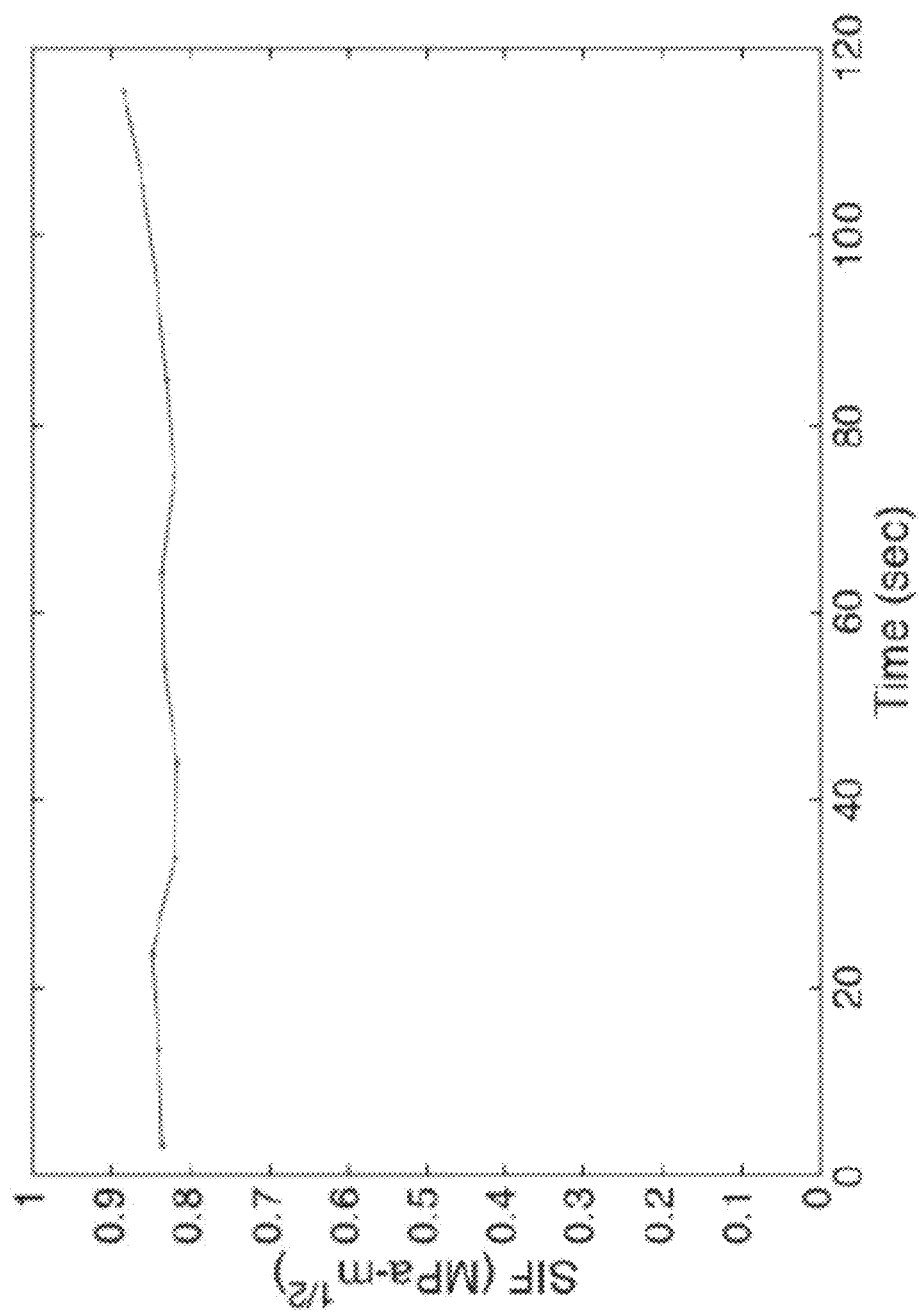
FIG. 4 illustrates a stress intensity factor for a homogeneous Homalite specimen.

The above steps can be applied to the images of crack propagation in a homogeneous Homalite specimen. An exemplary stress intensity factor is plotted in FIG. 4. As visible in FIG. 4, the stress intensity factor is quite stable in a homogeneous material as the crack propagates steadily through the specimen. This result is in agreement with findings regarding the properties of linear elastic fracture mechanics (LEFM), $K_I=\sqrt{G_c E}$ (which is a constant).

Figure 5:
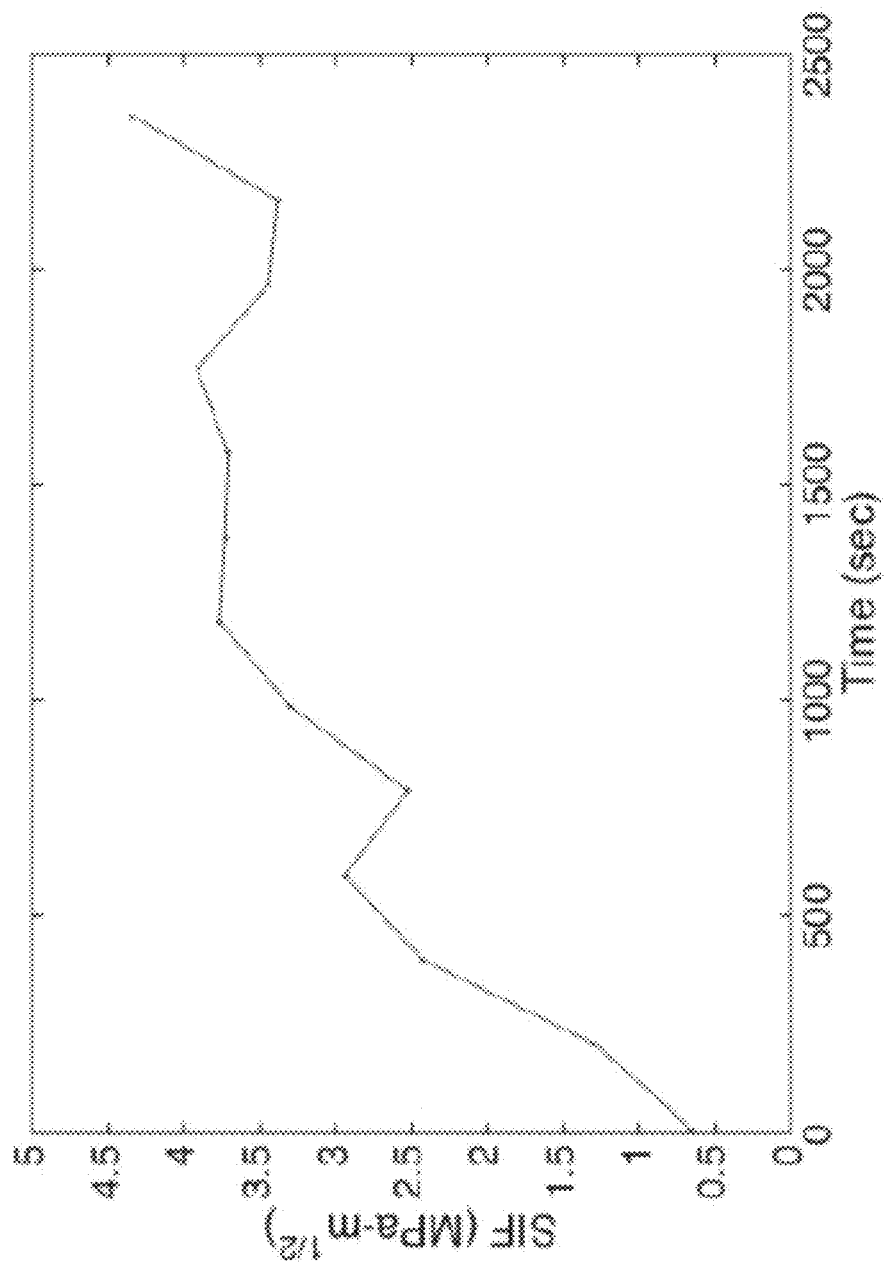
FIG. 5 illustrates a stress intensity factor for the crack tip when trapped in a hole.

The steps described above can be applied to specimens with holes (heterogeneity). It can be observed that when the crack tip is trapped in a hole, the driving force (or stress intensity factor) is increased dramatically as shown in FIG. 5. More energy needs to be applied to the crack tip for the crack to propagate, in these cases. Hence, the effective fracture toughness of this heterogeneous material is higher than that of the homogeneous material.

In the present disclosure, an experimental configuration and method are described, giving a steady macrosopic crack growth while letting the crack evolve freely microscopically. This method provides a good foundation to investigate fracture propagation in heterogeneous materials. The present disclosure also shows that the effective fracture toughness is increased by the holes (or heterogeneity) in the specimens. Heterogeneity thus has a profound effect on effective fracture toughness.

Figure 6:
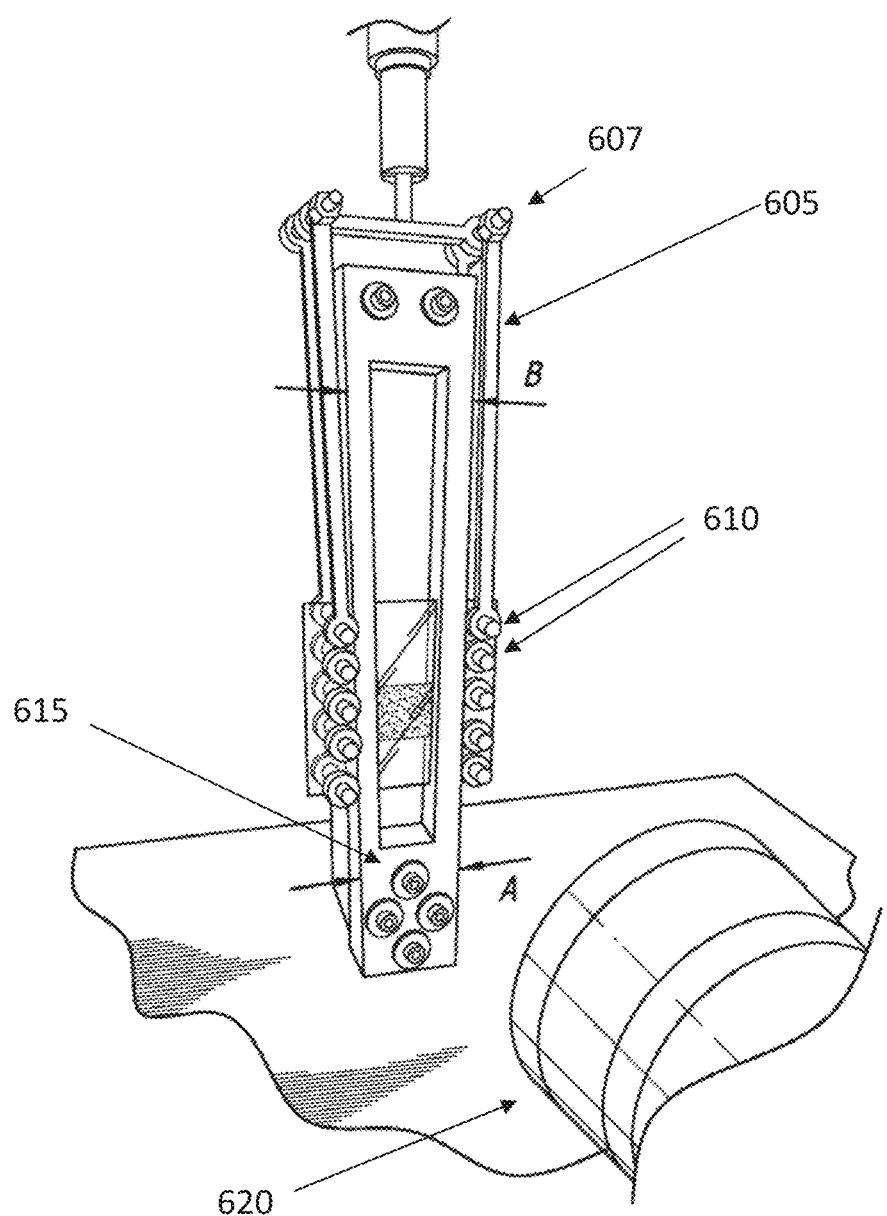
FIGS. 6-7 depict exemplary embodiments of a rail and roller.
Figure 7:
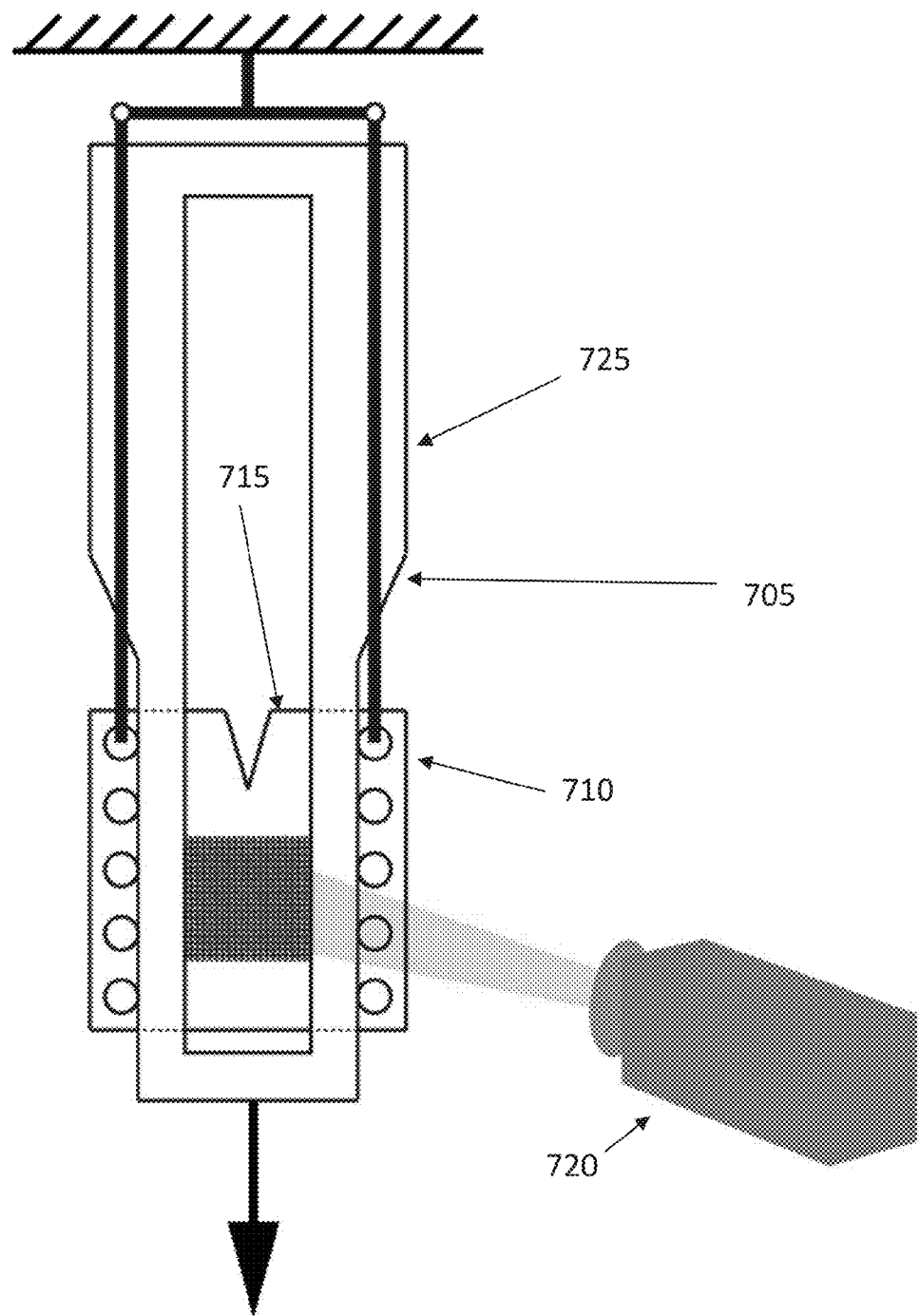

In some embodiments, instead of cables (120) as illustrated in FIG. 1, other linking parts may be used. For example, as visible in FIG. 6, a rigid linkage system may be used (605), as part of a frame to hold the specimen in place. The rollers (610), that is the rods inserted through the specimen, are attached to the rigid linkage arms. Although rigid, in some embodiments the linkage arms can rotate at the connecting point (617), to allow the specimen to be pulled apart. The rail (615) can be pushed down while the specimen is held in place, or the specimen can be pulled up while the rail is held fixed. In other embodiments, the rail can be pulled up while the specimen is held fixed, for example. In this alternative embodiment the shape of the rail is reversed in order to allow the rollers to fracture the specimen. In yet other embodiments, a no-contact method may be used, where either the rail or the specimen are moved through a magnetic force. In these embodiments, either the rail or the specimen are magnetic materials. All the above embodiments work on the basic operating principle of having a slope applying a force through movement of the rollers on the slope. The experimental setup forces the specimen over the rail and measures the energy release rate; this can be done with either a cable system or a linkage system. FIG. 7 illustrates an embodiment where the sloped region on the rail is visible (705). As the rollers move upward, or as the rail is pushed downward, the rollers enter the sloped region and pull the specimen (715) apart.

In some embodiments, the rail or specimen movement is controlled by a step motor. A camera (720) can be used to measure the specimen fracture. In some embodiments, it is possible to replace DIC with the grid method for measuring displacements. The grid method, for example, is described in Ref. [11]. In the grid method, a grid is either engraved, printed or transferred on to the specimen. The image of the grid before and after deformation is measured and these images are used to infer the displacement and strain fields. Various algorithms that enable the determination of displacement and strain fields are available. In some embodiments, it is possible to replace the global method described above with an area J-integral to calculate the energy release rate. The J-integral is a path integral to determine the energy release rate at a crack. However, in an experimental setting, a path integral is susceptible to significant errors due to noisy measurement of displacement and strain fields. Therefore, it is possible to convert the path integral to an area integral using the divergence theorem. Since the integration is over an area, the errors due to noisy measurements are averaged over and diminished. In some embodiments, it is possible to use the measured force to determine the energy release rate.

In some embodiments, the specimen is fixed and inserted in a slot in the rail in such a way as to be able to remain fixed while the rail is pushed down or pulled up. In other embodiments, the rail remains fixed while the specimen is moved. In other words, the specimen and rail move relative to each other, even as either the rail or specimen is fixed relative to the laboratory frame of reference.

As can be seen in FIG. 7, the rail has a sloped region (705). The rail of FIG. 6 can also be implemented in a similar manner. In other embodiments, the rail can also have sloped outer edges throughout its length, for example having a total lateral width A as visible in FIG. 6, while having a greater lateral width B at the top. A camera (620) can be used to observe the specimen while fracturing.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

1. Zehnder, A. T., *Fracture Mechanics*. Lecture Notes in Applied and Computational Mechanics. 2012: Springer.
2. Liang, F., et al., *Fracture Behavior of Flock Fiber Reinforced Laminar Composite*. Journal of Materials Science and Engineering B, 2011. 1(1): p. 1-13.
3. Kruzic, J. J., et al., *The Utility of R-Curves for Understanding Fracture Toughness-Strength Relations in Bridging Ceramics*. Journal of the American Ceramic Society, 2008. 91(6): p. 1986-1994.
4. Faber, K. T. and A. G. Evans, *Crack deflection processes-I. Theory*. Acta Metallurgica, 1983. 31(4): p. 565-576.
5. Gao, H. and J. R. Rice, *A first-order perturbation analysis of crack trapping by arrays of obstacles*. Journal of Applied Mechanics, 1989. 56(4): p. 828-836.
6. Bower, A. F. and M. Ortiz, *A three-dimensional analysis of crack trapping and bridging by tough particles*. Journal of the Mechanics and Physics of Solids, 1991. 39(6): p. 815-858.
7. Hutchinson, J. W. and Z. Suo, *Mixed mode cracking in layered materials*. Advances in applied mechanics, 1991. 29: p. 63-191.
8. Cox, B. and Q. Yang, *In quest of virtual tests for structural composites*. science, 2006. 314(5802): p. 1102-1107.
9. Hossain, M. Z., et al., *Effective toughness of heterogeneous media*. Journal of the Mechanics and Physics of Solids, 2014. 71: p. 15-32.

10. Mathieu, F., F. Hild, and S. Roux, *Identification of a crack propagation law by digital image correlation.* International Journal of Fatigue, 2012. 36(1): p. 146-154.

11. Badulescu C, Grediac M and J D Mathias, Measurement Science and Technology, Volume 20, Number 9, July 2009

What is claimed is:

1. A method comprising:
providing a specimen comprising at least a first and second hole;
inserting a first rod into the first hole and a second rod into the second hole;
attaching a first end of a cable to the first rod and a second end of the cable to the second rod;
providing a cable support;
placing a portion of the cable on the cable support;
providing a rail, the rail comprising at least two sloped regions angled away from a longitudinal axis and configured to laterally displace the first and second rod relative to each other;
inserting the specimen in the rail; and
applying a time-dependent displacement boundary condition to the specimen by gradually moving the rail away from the cable support, thereby applying a displacing force to the first and second rods through the at least two sloped regions and causing the specimen to fracture.

2. The method of claim 1, wherein the at least first and second holes are at symmetric positions relative to a central axis of the specimen.

3. The method of claim 1, wherein the rail and the cable support are centered along a central axis of the specimen.

4. The method of claim 1, further comprising providing a camera to record images of a developing fracture in the specimen.

5. The method of claim 4, further comprising measuring an effective fracture toughness of the specimen.

6. The method of claim 5, wherein the measuring the effective fracture toughness is by analyzing the recorded images.

7. The method of claim 1, further comprising measuring a macroscopic energy release rate for a fracture in the specimen.

8. The method of claim 1, wherein applying a time-dependent displacement boundary condition comprises applying a macroscopically steady crack growth at a fracture location in the specimen.

9. The method of claim 4, further comprising applying a random fine speckle pattern to the specimen and observing a deformation of the random fine speckle pattern with the camera.

10. The method of claim 9, further comprising:
calculating an original position and a deformed position for a plurality of pixels in a recorded image;
interpolating a deformed position for pixels inbetween the calculated pixels;
calculating a cost function, the cost function based on a difference between the recorded image and a deformed reference image;
minimizing the cost function with respect to a stress intensity factor and crack tip position.

11. The method of claim 10, wherein the deformed reference image is based on a given stress intensity factor and a given crack tip position.

12. The method of claim 11, wherein the specimen is heterogeneous.

13. The method of claim 4, further comprising applying a grid pattern to the specimen and observing a deformation of grid pattern with the camera.

14. A method comprising:
providing a specimen comprising at least a first and second hole;
inserting a first rod into the first hole and a second rod into the second hole;
attaching the first rod and the second rod to rigid linkage arms;
providing a rail, the rail comprising at least two sloped regions angled away from a longitudinal axis and configured to laterally displace the first and second rod relative to each other;
inserting the specimen in the rail; and
applying a time-dependent displacement boundary condition to the specimen by gradually moving the rail and the specimen relative to each other, thereby applying a displacing force to the first and second rods through the at least two sloped regions and causing the specimen to fracture.

15. The method of claim 14, wherein the gradually moving the rail and the specimen relative to each other is by moving the rail while keeping the specimen at a fixed position, or by moving the specimen while keeping the rail at a fixed position.

16. The method of claim 15, further comprising providing a camera to record images of a developing fracture in the specimen.

17. The method of claim 16, further comprising measuring an effective fracture toughness of the specimen.

18. The method of claim 17, wherein the measuring the effective fracture toughness is by analyzing the recorded images.

19. The method of claim 16, further comprising applying a random fine speckle pattern to the specimen and observing a deformation of the random fine speckle pattern with the camera.

20. The method of claim 14, wherein applying a time-dependent displacement boundary condition comprises applying a macroscopically steady crack growth at a fracture location in the specimen.

* * * * *